US010387586B2

(12) United States Patent
Li et al.

(10) Patent No.: US 10,387,586 B2
(45) Date of Patent: Aug. 20, 2019

(54) METHOD FOR EARLY WARNING ANALYSIS OF EUTROPHICATION OF DESIGNED ARTIFICIAL WATER BODY

(71) Applicant: Urban Planning & Design Institute of Shenzhen, Guangdong (CN)

(72) Inventors: Xiaojun Li, Guangdong (CN); Feng Li, Guangdong (CN); Lu Yu, Guangdong (CN); Yan Du, Guangdong (CN); Nian Ding, Guangdong (CN)

(73) Assignee: Urban Planning & Design Institute of Shenzhen, Shenzhen, Guangdong (CN)

( * ) Notice: Subject to any disclaimer, the term of this patent is extended or adjusted under 35 U.S.C. 154(b) by 407 days.

(21) Appl. No.: 15/113,595

(22) PCT Filed: Jan. 12, 2015

(86) PCT No.: PCT/CN2015/070514
§ 371 (c)(1),
(2) Date: Jul. 22, 2016

(87) PCT Pub. No.: WO2015/109957
PCT Pub. Date: Jul. 30, 2015

(65) Prior Publication Data
US 2017/0004236 A1 Jan. 5, 2017

(30) Foreign Application Priority Data
Jan. 23, 2014 (CN) .......................... 2014 1 0033490

(51) Int. Cl.
*G06F 17/50* (2006.01)
*G02F 1/00* (2006.01)
(Continued)

(52) U.S. Cl.
CPC ............ *G06F 17/5009* (2013.01); *C02F 1/00* (2013.01); *C11D 3/10* (2013.01); *G06F 17/5004* (2013.01);
(Continued)

(58) Field of Classification Search
CPC .... G06F 17/5009; G02F 1/00; G01N 33/1806
(Continued)

(56) References Cited

U.S. PATENT DOCUMENTS

2005/0183331 A1 8/2005 Kania et al.
2005/0273358 A1* 12/2005 Zimmerman .......... G06Q 10/04
705/308

(Continued)

FOREIGN PATENT DOCUMENTS

| CN | 101234821 A | 8/2008 |
| CN | 102542108 A | 7/2012 |
| CN | 103177303 A | 6/2013 |

OTHER PUBLICATIONS

International Search Report for PCT/CN2015/070514 dated Mar. 17, 2015.

*Primary Examiner* — Thai Q Phan
(74) *Attorney, Agent, or Firm* — McCormick, Paulding & Huber LLP

(57) ABSTRACT

The present invention relates a method for early warning analysis of eutrophication of a designed artificial water body, comprising: establishing a three-dimensional model of the designed artificial water according to the data corresponding to a planning scheme of the water body, wherein the three-dimensional model of the designed artificial water body comprises at least the designed artificial water body and surrounding buildings; according to the three-dimensional model of the designed artificial water body, analyzing the designed artificial water body through an ecological simulation technology to obtain at least one of the analysis (Continued)

results including hydrological mobility, hydraulic retention time, algal community composition of source water, designed water depth, water body surface wind field, solar radiation and temperature of the designed artificial water body; and assessing the risk of eutrophication of the designed artificial water body according to at least one of the analysis results of the ecological simulation.

19 Claims, 13 Drawing Sheets

(51) Int. Cl.
*G06Q 50/00* (2012.01)
*C02F 1/00* (2006.01)
*C11D 3/10* (2006.01)
*G01N 33/18* (2006.01)

(52) U.S. Cl.
CPC .......... *G06Q 50/00* (2013.01); *C02F 2209/00* (2013.01); *C02F 2209/005* (2013.01); *G01N 33/1806* (2013.01)

(58) Field of Classification Search
USPC .................. 703/2, 6; 705/308, 314; 702/2; 73/61.65
See application file for complete search history.

(56) References Cited

U.S. PATENT DOCUMENTS

| 2009/0222307 | A1* | 9/2009 | Beaver | G06Q 10/06 705/7.25 |
| 2012/0004938 | A1* | 1/2012 | Beaver | G06Q 10/00 705/7.11 |
| 2012/0185170 | A1* | 7/2012 | Miskewitz | G01N 33/1806 702/2 |

* cited by examiner

Establishing a three-dimensional model of a designed artificial water body according to the data corresponding to a planning scheme of the water body, comprising at least the designed artificial water and surrounding buildings.

Analyzing the designed artificial water body through an ecological simulation technology according to the three-dimensional model of the designed artificial water body, to obtain at least one of the analysis results including hydrological mobility and hydraulic retention time, algae community composition of source water, designed water depth, water body surface wind field, solar radiation and temperature of the designed artificial water body Assessing the risk of eutrophication of the designed artificial water body according to at least one of the analysis results of ecological simulation

Fig. 1

By taking the designed artificial water body as an analysis range, extending a first distance from the boundary to the periphery, to determine a modeling range of the three-dimensional model, wherein the first distance is a distance from the water boundary of the designed artificial water body to the center of the designed artificial water body Establishing the three-dimensional model of the designed artificial water body by Sketchup, CAD or GIS software according to the bottom topography and the water body depth of the designed artificial water body, wherein the water surface of the designed artificial water body and the bottom of the surrounding buildings are at the same level

Fig. 2

METHOD FOR EARLY WARNING ANALYSIS OF EUTROPHICATION OF DESIGNED ARTIFICIAL WATER BODY

CROSS-REFERENCE TO RELATED APPLICATIONS

This application is entitled to the benefit of and incorporates by reference subject matter disclosed in the International Patent Application No. PCT/CN2015/070514 filed on Jan. 12, 2015 and Chinese Patent Application No. 201410033490.5 filed on Jan. 23, 2014.

TECHNICAL FIELD

The present invention relates to the technical field of urban planning and design, and particularly to a method for early warning analysis of eutrophication of a designed artificial water body.

BACKGROUND

With rapid development of economy, the urbanization process in China is accelerated. In the context of continuous land expansion, increasing attentions are paid to the ecological environment. In most regions, artificial lakes or small-sized tributaries have been designed in the process of urban planning under the consideration of constructing an ecological security pattern and improving regional landscapes. Generally the artificial lakes or small-sized tributaries are small in area, low in water storage capacity and poor in hydrological mobility, and are in a relative static state in most situations. These characteristics lead to serious eutrophication problems for the small-sized artificial lakes and relatively static tributaries within two or three years after they are built.

At present, in the aspect of the research of water body eutrophication, the applications incorporating with software are mainly the ELCOM-CAEDYM model, or the fluid dynamics combining with remote sensing and computation. The applications in this field mainly considerate hydrometeorology conditions such as water load, solar radiation, temperature, humidity, wind direction, wind velocity and rainfall, etc., and zooplankton and phytoplankton, simulation research is conducted on the current eutrophication and temperature stratification of the water body and the resulting data is compared with the measured data, and thus the correlation analysis on the contents of chlorophyll a, nitrogen and phosphorus, and the eutrophication condition is achieved. The technical means in the research of the water body eutrophication are substantially used for lakes, reservoirs and gulfs which already exist, and the parameters are required to be accurate in detail, such as actual concentration of nitrogen, phosphorus and chlorophyll a, extinction coefficient of the water body, and the surface reflectivity of long-wave radiation, etc., so it is difficult to achieve such type of data in the planning and design stage.

The introduction of artificial water body in the process of urban planning has been becoming a common design means. The eutrophication degree of the artificial water body after construction is highly concerned by environmentalists. However, for the water body which is currently in the plan only, its eutrophication range and degree cannot be predicted at the planning and design stage at present; only the point source and area source pollutions can be preliminarily estimated based on the surrounding situations and the planning land utilization type to formulate relevant planning and control measures for pollution interception.

SUMMARY

To solve the above-mentioned technical problems, the present invention provides a method for early warning analysis of eutrophication of a designed artificial water body, which can assess the risk of eutrophication of the designed artificial water body in the urban planning and design stage, thereby providing a basis for preventing and controlling the eutrophication of the designed artificial water body.

A technical solution adopted in the present invention comprises: establishing a three-dimensional model of a designed artificial water body according to data corresponding to a planning scheme of the water body, wherein the three-dimensional model at least comprises the designed artificial water and surrounding buildings; analyzing the designed artificial water body through an ecological simulation technology according to the three-dimensional model of the designed artificial water body, to obtain at least one of the analysis results including hydrological mobility and hydraulic retention time, algae community composition of source water, designed water depth, water body surface wind field, solar radiation and temperature of the designed artificial water body; and assessing the risk of eutrophication of the designed artificial water body according to at least one of the analysis results of ecological simulation.

Further, the step of analyzing the designed artificial water body through an ecological simulation technology according to the three-dimensional model of the designed artificial water body comprises: analyzing the water body surface wind field distribution of the designed artificial water body by means of physical environment simulation analysis software to obtain a wind disturbance region and a wind calm region of the designed artificial water body, thereby to preliminarily obtain an eutrophication influence region and a eutrophication prevention and control region for it, wherein the wind disturbance region is a main region where microalgae are generated, the wind calm region and downwind bays and tributaries are main regions where microalgae are generated and aggregated, the wind disturbance region is a eutrophication prevention and control region for the designed artificial water body, and the wind calm region and downwind bays and tributaries are eutrophication influence regions for the designed artificial water body.

Further, the step of analyzing the designed artificial water body through an ecological simulation technology according to the three-dimensional model of the designed artificial water body comprises: conducting solar radiation analysis on the surface of the designed artificial water body by the physical environment simulation analysis software according to an simulation analysis of annual solar radiation and shadow variation, to obtain a region not shaded by the surrounding buildings in the designed artificial water body, which is an solar radiation region and a eutrophication-prone region for the designed artificial water body is to occur.

Further, the step of analyzing the designed artificial water body through an ecological simulation technology according to the three-dimensional model of the designed artificial water body comprises: conducting a temperature and microalgae reproduction relationship analysis on the designed artificial water body, analyzing the spatial distribution difference of the water temperature of the designed artificial water body through the physical environment simulation analysis software, to determine the influence of the spatial distribution difference of the water temperature of the designed artificial water body on the distribution of microalgae within the designed artificial water body.

Further, the step of analyzing the designed artificial water body through an ecological simulation technology according to the three-dimensional model of the designed artificial water body comprises: conducting microalgae species analysis on the designed artificial water body, and particularly analyzing the dominant microalgae species from a water body around the designed artificial water body or a water body of a water source and corresponding climate conditions, to obtain the microalgae species for eutrophication which may potentially occur in the designed artificial water body and the corresponding climate conditions suitable for the growth of the potential microalgae species.

Further, the step of analyzing the designed artificial water body through an ecological simulation technology according to the three-dimensional model of the designed artificial water body comprises: conducting hydrological mobility and hydraulic retention time analysis on the designed artificial water body, to estimate the possibility and the degree of eutrophication of the designed artificial water body, wherein: when the water body area of the designed artificial water body is larger, the threshold of the hydraulic retention time is longer, and when the water body area is smaller, the threshold of hydraulic retention time is shorter; a flow rate of the designed artificial water body greater than 0.4 m/s indicates that the designed artificial water body is not eutrophication-prone, and a flow rate of the designed artificial water body less than or equal to 0.4 m/s indicates that the designed artificial water body is eutrophication-prone; and the higher the water body connectivity rate of the designed artificial water body is, the less the eutrophication of the designed artificial water body is.

Further, the step of analyzing the designed artificial water body through an ecological simulation technology according to the three-dimensional model of the designed artificial water body comprises: conducting a designed water depth and wind disturbance analysis on the designed artificial water body, to determine the influence of nutrients in the designed artificial water body on the microalgae reproduction, wherein for the shallow-water type designed artificial water body, wind disturbance is beneficial to the thorough mixing of nutrients in the designed artificial water body, and thus is beneficial to the microalgae reproduction; for a deep-water type designed artificial water body, the wind would result in a temperature decrease and a disturbance of the still state of the surface water and then restrain the reproduction of phytoplankton in the water body.

Further, the step of establishing the three-dimensional model of the designed artificial water body according to the data corresponding to the planning scheme of the water body comprises: by taking the designed artificial water body as an analysis range, extending a first distance from the boundary to the periphery, to determine a modeling range of the three-dimensional model, wherein the first distance is a distance from the water boundary to the center of the designed artificial water body; and establishing the three-dimensional model of the designed artificial water body by Sketchup, CAD or GIS software according to the bottom topography and the water body depth of the designed artificial water body, wherein the surface of the designed artificial water body and the bottom of the surrounding buildings are at the same level.

Further, when the assessment results indicate that there are high risk regions of eutrophication in the designed artificial water body, the method further comprises: determining corresponding strategies for preventing and controlling the possible eutrophication in the designed artificial water body according to the possibility and severity of the eutrophication in the designed artificial water body, and returning an adjustment for reassessment, until the assessment results indicate that the high risk regions of eutrophication in the designed artificial water body are significantly reduced.

Further, the physical environment simulation analysis software comprises physical environment simulation analysis software such as Fluent, Phoenics, AirPak, CFDRC or Ecotect Analysis.

The beneficial effects of the present invention include: different from the prior art, the present invention, by establishing the three-dimensional model of the designed artificial water body, and analyzing the designed artificial water body through an ecological simulation technology, can obtain at least one of the analysis results including hydrological mobility and hydraulic retention time, algae community composition of source water, designed water depth, water body surface wind field, solar radiation and temperature of the designed artificial water body, thereby evaluating the risk of eutrophication of the designed artificial water body. In this way, the risk of eutrophication of the designed artificial water body can be assessed in the urban planning and designing stage, thereby providing a basis for preventing and controlling eutrophication of the designed artificial water body.

DESCRIPTION OF THE DRAWINGS

FIG. 1 is a flow diagram of a method for early warning analysis of eutrophication of a designed artificial water body in an embodiment according to the present invention;

FIG. 2 is a flow diagram of Step S101 shown in FIG. 1;

DETAILED DESCRIPTION

Figure 3:
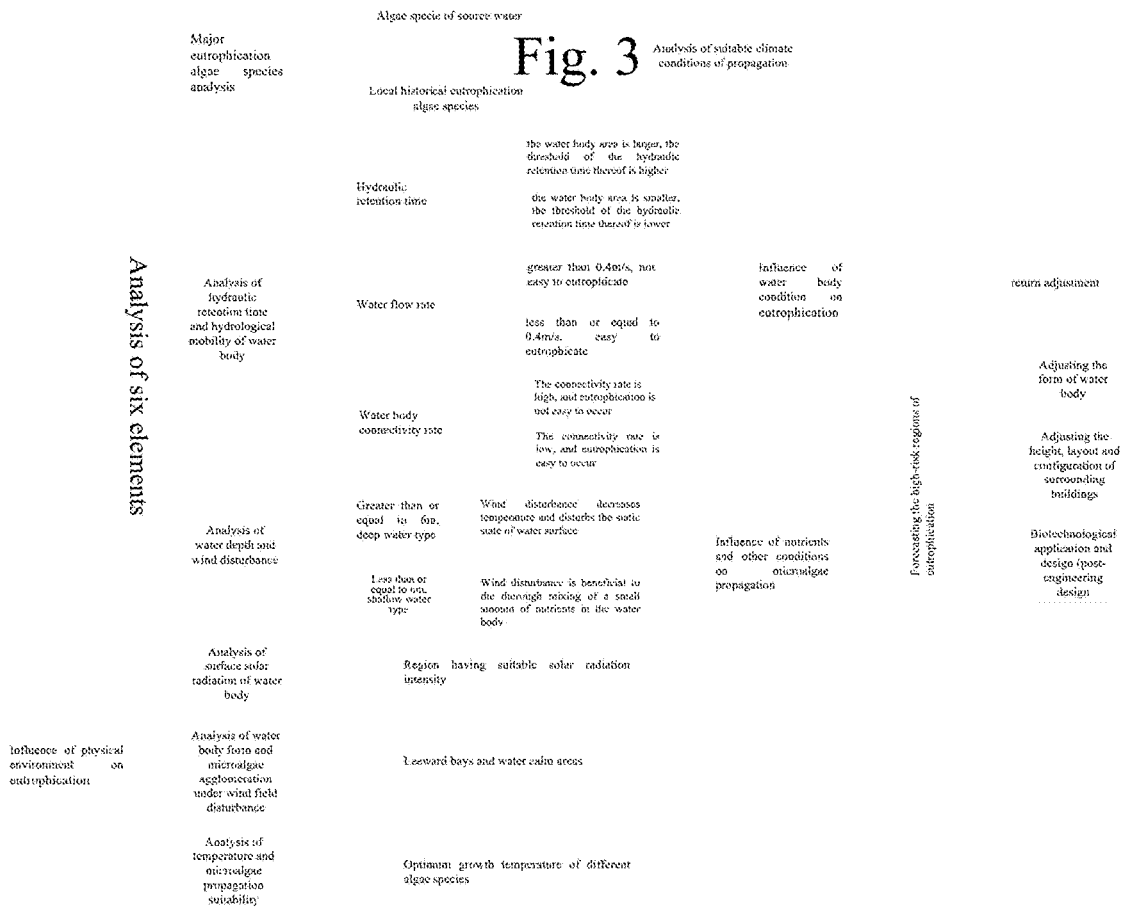
FIG. 3 is a flow diagram of a method for early warning analysis of eutrophication of a designed artificial water body in a specific embodiment according to the present invention.

First of all, the basic principles of ecology for water body eutrophication will be described below.

Eutrophication refers to a phenomenon that the contents of nutrients in water, such as nitrogen, phosphorus, etc., which are required for plant growth, are increased due to natural factors or disturbance of human activities, and as the temperature and solar radiation conditions meet the requirements, the microalgae or waterweeds in the water body reproduce rapidly, causing oxygen deficit of water body and gradual death of the living organisms in water, and thus producing peculiar smell and adverse effects on the landscape of the water body.

Eutrophication is caused by internal factors of the water body (for example, biological community composition, microalgae species, content of nutrients in water and movement of water body, etc.) and external factors (for example, pollutants, temperature, solar radiation and wind force, etc.), wherein climate factors and sudden external contaminants are usually main inducting factors for eutrophication. Especially in spring and summer, due to increased temperature, in the water body thermodynamic motion is strengthened and nutrients are fully mixed, and the climate conditions suitable for the growth of microalgae are reached, phenomenon of eutrophication is prone to occurring.

Most of eutrophication is represented as the algae bloom. Dissolved oxygen in water is continuously consumed by the rapidly propagated microalgae; moreover, with short growth cycles, microalgae and other planktons are either decomposed by aerobe or anaerobe after death, thereby continuously producing toxic gases such as hydrogen sulfide, etc.; the microalgae of some species may release biotoxin at the growth or decomposed stage, poisoning aquatic animals. Resulting from above phenomena, the water quality is deteriorated, and mass death of fish and other aquatic organisms is incurred. In the process of decay of the microalgae and other plankton residues, amount of nutrient elements such as nitrogen, phosphorus, etc. are released into water, and used by new generations of microalgae or other organisms. Therefore, for the eutrophicated water body, even if the external source of nutrient substance is cut off, it is still difficult for the water body to self-purify and return to its normal state.

Therefore, an optimal method for controlling eutrophication is to prevent the occurrence of eutrophication or reduce the degree of eutrophication. For artificially constructed water body, the most economical and effective means is to prevent and control eutrophication at the design stage.

The present invention is described below in detail with reference to the drawings and embodiments.

Referring to FIGS. 1 and 2, which are the flow diagrams of two embodiments of a method for early warning analysis of eutrophication of a designed artificial water body according to the present invention, the method comprises:

Step S101: establishing a three-dimensional model of a designed artificial water body according to data corresponding to a planning scheme of the water body, wherein the three-dimensional model of the designed artificial water body comprises at least the designed artificial water body and surrounding buildings.

As a polygon representation of an object, the three-dimensional model is usually displayed by means of a computer or other video devices. The displayed object can be a real object in the real world, or an imaginary object. All things existing in the physical natural world can be represented by a three-dimensional model. The three-dimensional model often can be generated by means of special software for three-dimensional modeling tool, or by other methods. As the data sets of points and other information, the three-dimensional model can be manually generated, or can be generated in accordance with a certain algorithm. At present, there are three modeling methods in general including: the first method—modeling by use of three-dimensional software, the second method—modeling through measurement of instruments and devices, and the third method—modeling using images or videos.

In general, there is a planning scheme for an artificial water body before it is constructed, therefore a three-dimensional model of the designed artificial water body can be established according to the data from the planning scheme. Since the surrounding buildings have influences on the solar radiation of the designed artificial water body, the three-dimensional model of the designed artificial water body comprises at least the designed artificial water body and surrounding buildings, and can comprise road layout or other objects as well.

Specifically, with reference to FIG. 2, Step S101 comprises a sub-step S101*a* and a sub-step S101*b*.

Sub-step S101*a*: by taking the designed artificial water body as an analysis range, extending a first distance from the boundary towards the periphery, to determine a modeling range for the three-dimensional model, wherein the first distance is a distance from the water boundary to the center of the designed artificial water body.

Sub-step S101*b*: according to the bottom topography and the water body depth of the designed artificial water body, establishing the three-dimensional model of the designed artificial water body by Sketchup, CAD or GIS software, wherein the surface of the designed artificial water body and the bottom of the surrounding buildings are at the same level.

A relatively accurate three-dimensional model can be established through the Sketchup, CAD or GIS software.

Step S102: according to the three-dimensional model of the designed artificial water body, analyzing the designed artificial water body through an ecological simulation technology so as to obtain at least one of the following analysis results: hydrological mobility and hydraulic retention time, algae community composition of source water, designed water depth, water body surface wind field, solar radiation and temperature of the designed artificial water body.

The simulation technology refers to an experimental method for establishing a model (such as image model, descriptive model or mathematical model) of a research object using similar principles, and indirectly researching the prototype regularity through the model. The major ecological simulation parameters for the ecological simulation technology include environment light simulation, environment noise simulation, visibility simulation and environment wind simulation, etc. In practical application, the ecological simulation technology is mainly used for simulating and analyzing noise distribution, sunshine and shielding durations, solar radiation intensity, visibility and wind environment (wind velocity, wind pressure, coefficient of wind stress, effects of wind shear on water column, wind-derived surface currents and weak wind region analysis) through professional physical environment simulation analysis software, whereby to optimize the scheme and layout according to the obtained results.

As mentioned above, the influence factors of water body eutrophication mainly include internal and external factors, wherein the internal factors may include: biological community composition, microalgae species, content of nutrients in water body and movement of water body, etc.; and the external factors may include: pollutants, temperature, solar radiation, wind force, etc. According to the three-dimensional model of the designed artificial water body, the designed artificial water body is analyzed through an ecological simulation technology so as to obtain at least one of the analysis results including hydrological mobility, hydraulic retention time, algae community composition of source water, designed water depth, water body surface wind field, solar radiation and temperature of the designed artificial water body to facilitate the assessment of risk of eutrophication in the water body.

In practical application, after an analysis model (including three-dimensional models of surrounding buildings and roads) of the designed artificial water body is established, it is then introduced into a physical environment simulation analysis software, in which a physical environment analysis model is established according to the simulation requirements and boundary conditions and initial parameters of simulation are set. For example, the simulation is conducted by the Phoenics software, and additionally SUN, WIND, PLATE, and GRASS modules are required to be configured besides the modules of the constructed water bodies, buildings and roads. It is difficult to meet the temperature conditions required for the growth of microalgae due to the average temperature in winter is relatively low, therefore the phenomenon of water body eutrophication mainly occurs in three seasons, i.e. spring, summer and autumn, and is relatively serious in summer. According to local actual meteorological data, boundary conditions of the model are configured, including air temperature, air pressure, wind velocity, wind direction, solar radiation intensity and ground roughness, to establish the corresponding simulation models of wind direction and velocity. Meanwhile, the water temperature conditions of original lakes or rivers around the designed artificial water body are analyzed, and related parameters including water temperature, emissivity, heat transfer coefficients, etc. of lakes are configured according to the needs for simulation.

Step S103: according to at least one of the analysis results of the ecological simulation, assessing the risk of eutrophication of the designed artificial water body.

The risk of eutrophication of the designed artificial water body is evaluated according to at least one of the analysis results of ecological simulation. The analysis result of the ecological simulation which contains more influence factors of the water body eutrophication is more accurate in the evaluation of eutrophication risk of the designed artificial water body assessed.

In brief, in the embodiment of the present invention, by establishing the three-dimensional model of the designed artificial water body, and analyzing the designed artificial water body through an ecological simulation technology, at least one of the analysis results including hydrological mobility, hydraulic retention time, algae community composition of source water, designed water depth, water body surface wind field, solar radiation and temperature of the designed artificial water body can be obtained, whereby to evaluate the risk of eutrophication of the designed artificial water body. In this way, the risk evaluation of eutrophication of the designed artificial water body in the urban planning and design can be done, whereby to provide a basis for preventing and controlling eutrophication of the designed artificial water body.

In the above-mentioned step S102, according to the three-dimensional model of the designed artificial water body, the designed artificial water body is analyzed through an ecological simulation technology so as to obtain at least one of the analysis results including hydrological mobility, hydraulic retention time, algae community composition of source water, designed water depth, the water body surface wind field, solar radiation and temperature of the designed artificial water body (please see FIG. 3 for more information). By means of the embodiment in FIG. 3, the six analysis results including hydrological mobility, hydraulic retention time, algae community composition of source water, designed water depth, water body surface wind field, solar radiation and temperature of the designed artificial water body can be combined, in consideration of the risk of eutrophication of the designed artificial water body. Of course, the analysis methods for any single one or more of the analysis results described above are the same, which will not be repeatedly described herein separately.

A specific embodiment of a method for early warning analysis of eutrophication of a designed artificial water body according to the present invention is as shown in FIG. 3, comprising the following steps:

Step S201: conducting water body eutrophication algae species analysis on the designed artificial water body, specifically analyzing the microalgae species from a water body around the designed artificial water body or a water body of a water source in which eutrophication occurs and a corresponding climate condition, to obtain the potential microalgae species from the designed artificial water body in which eutrophication may occur and the corresponding climate condition suitable for the growth for the potential microalgae species Different water body surface wind fields have different influence on the mass propagation of different species of microalgae. Therefore, the dominant microalgae species causing eutrophication in surrounding lakes or other fresh water bodies near the designed artificial water body and the corresponding climate conditions must be analyzed firstly, for example, water temperature, air temperature, solar radiation, wind direction and wind velocity data at the time of water bloom occurring. Especially, the historical eutrophication data of the water source of the incoming water of the designed artificial water body is analyzed, to obtain the dominant algae species of the source water.

For example, among the most common microalgae species for eutrophication: cyanobacteria, microcystis, diatom or filamentous algae (green algae, blue-green algae, yellow-green algae), the planktonic blue-green algae and microcystis are calm-wind-loving type microalgae, and the disturbance of wind to the water body can suppress the reproduction of such microalgae. However, slightly flowing water is beneficial to the rapid propagation and proliferation of diatom and filamentous algae. In general, diatom is a food source for aquatic animals, the water can be purified by the filamentous algae attached to the bottom of a lake. The algal bloom of diatom or filamentous algae emerges only in some extreme cases, producing sensory pollution of landscape. Moreover, blue-green algae and microcystis are the common algae species for algal bloom, and easily produce biotoxin, having great damage to the aquatic ecosystem.

By analyzing the algae species of the designed artificial water body, the common algae species contributing to eutrophication of the designed artificial water body and the climate conditions suitable for the growth of the algae are identified.

Step S202: conducting hydrological mobility and hydraulic retention time analysis on the designed artificial water body, to determine the occurrence possibility of eutrophication and the degree of eutrophication to the designed artificial water body, wherein: when the area of the water body of the designed artificial water body is relatively large, the threshold of the hydraulic retention time is relatively high, and when the water body area is relatively small, the threshold of the hydraulic retention time is relatively low; a flow rate of the designed artificial water body greater than 0.4 m/s indicates that the designed artificial water body is not eutrophication-prone, and a flow rate of the designed artificial water body less than or equal to 0.4 m/s indicates that the designed artificial water body is eutrophication-prone; and a higher water body connectivity rate of the designed artificial water body indicates that the designed artificial water body is less eutrophication-prone.

The analysis of the mobility of the designed artificial water body specifically comprises the analysis of the connectivity between the designed artificial water body and the upstream and downstream adjacent water bodies, and the analysis of the water flow quantity and flow rate of the water source. The analysis of the hydraulic retention time is considered, if the water body is a relatively closed designed artificial water body.

It is found in related research that when the flow rate of a natural water body is 0.4 m/s, the growth of microalgae and the occurrence of water bloom are obviously suppressed by the movement of the water body. The critical value for occurrence of water bloom is 0.4 m/s. Therefore, the flow rates of the designed artificial water body greater than 0.4 m/s indicate that the designed artificial water body is not eutrophication-prone, and the flow rates of the designed artificial water body less than or equal to 0.4 m/s indicate that the designed artificial water body is eutrophication-prone; and the higher the water body connectivity rate of the designed artificial water body is, the less eutrophication-prone the designed artificial water body is. The threshold of hydraulic retention time refers to the period of changing water of the water body to prevent eutrophication of the water body. When the water body area of the designed artificial water body is relatively large, the threshold of the hydraulic retention time thereof is high, and when the water body area is relatively small, the threshold of the hydraulic retention time thereof is low. For the large-sized lakes such as Poyang Lake, Dongting Lake, Tai Lake, Hongze Lake and Chao Lake in the Yangtze River basin region, the water renewal periods are 57 days, 20 days, 309 days, 35 days and 168 days respectively, wherein Tai Lake and Chao Lake are seriously eutrophicated, and the other are partially eutrophicated.

Therefore, the severity of eutrophication of the designed artificial water body can be preliminarily determined by analyzing the designed hydraulic retention time and the water flow quantity and flow rate of the water source.

Step S203: Conducting designed water depth and wind disturbance analysis on the designed artificial water body, to determine the influence of nutrients in the designed artificial water body on the propagation of microalgae, wherein: for the shallow-water type designed artificial water body, wind disturbance is beneficial to the thorough mixing of nutrients in the designed artificial water body, which is beneficial to the propagation of microalgae; and for the deep-water type designed artificial water body, wind disturbance is beneficial to the reduction of the content of nutrients in the designed artificial water body, which is not beneficial to the propagation of microalgae.

Wind disturbance has different influences on the shallow-water type water body and the deep-water type water body, and especially has a significant different influence on lakes. A water body with the water depth of less than 6 m belongs to a shallow-water type water body, and a water body with the water depth of greater than 6 m belongs to a deep-water type water body.

The phenomenon of temperature stratification is common in deep-water type water bodies. In addition, at the bottom of a deep-water type water body, there is oxygen deficit, and P—Fe complex is unstable and easy to decompose, therefore the phosphorus in the sediment is released, leading to the increasing the concentration of the dissolved phosphorus in the water body. Wind disturbance contributes to breaking the phenomenon of temperature stratification, and can bring the surface water body with higher dissolved oxygen into the bottom layer. In the oxygen-rich state, a complex is formed by ferric and phosphorus, reducing the phosphorus dissolved in the water body. However, in a freshwater ecosystem, nitrogen is usually in a saturation state, and the content of phosphorus is often a limiting factor for the occurrence of eutrophication phenomenon. Once the concentration of the soluble phosphorus in the water body is increased, microalgae will reproduce rapidly under suitable solar radiation and temperature conditions.

In general, all the designed artificial water bodies belong to the shallow-water type water bodies, and most of the shallow-water type water bodies do not have stratification or only have transitory thermal stratification. Generally, in the bottom layer of a shallow-water type water body there will not be oxygen deficit, so the sediment such as humus, etc. are usually completely decomposed, and the water body of the surface layer is subjected to wind disturbance and thus the mixing of the upper and the lower layers of the water body is promoted, beneficial to the floating of bottom-layer nutrients. In addition, it is beneficial to the propagation of microalgae at a suitable temperature due to the sufficient solar radiation intensity on the surface layer.

Therefore, for the designed artificial shallow-water type water bodies, in view of the analysis of the mixing of nutrients, wind disturbance is beneficial to the propagation of microalgae. However, it is still necessary to conduct analysis according to different microalgae species. Generally, driven by the wind, the massively propagated microalgae will not stay in the water area of initial propagation, but will aggregate in a certain region of the water surface.

Step S204: conducting solar radiation analysis on the surface of the designed artificial water body by the physical environment simulation analysis software according to the simulation analysis of annual solar radiation and shadow variation, to obtain a region not shadowed by the surrounding buildings in the designed artificial water body, wherein the region not shadowed by the surrounding buildings in the designed artificial water body is an solar radiation region, which is the region where eutrophication of the designed artificial water body is prone to occur.

Solar radiation is an indispensable ecological factor for photosynthesis, chlorophyll synthesis, and the growth and propagation of microalgae, and is a major energy source of growth. Different species of microalgae have different photopic ranges, for example, blue-green algae in water adjusts its buoyancy through the synthesis and decomposition of carbohydrate under high-intensity solar radiation, whereby to perform a vertical movement to prevent from damage by high-intensity solar radiation. The solar radiation intensity on the surface of the water body has an influence on the propagation of microalgae, so the non-shadowed regions are beneficial to the water body eutrophication.

Therefore, in the analysis of the physical environment simulation analysis software, by simulating the annual solar radiation and shadow variation (for example simulating using the Ecotect Analysis software), a region of the designed artificial water body which is not shadowed by the surrounding buildings can be obtained, and in view of solar radiation, this region is eutrophication-prone.

The physical environment simulation analysis software includes Fluent, Phoenics, AirPak, CFDRC or Ecotect Analysis, and the like. Such software is mainly applied in industrial design, for example, chemical industry, combustion, explosion, ship and water conservancy, chemical reaction, fluid machinery and metallurgy, magnetic fluid, aerospace, automobile design, oil and natural gas and turbine design. In addition, it is used for building ventilation, building and surrounding environment analysis in the urban planning and design industry. However it is not found in the field of researching and planning for an ecosystem of a water body, especially for a water body which is in a specific region and in a planning and design condition but has not been constructed yet.

Step S205: analyzing the distribution of a water body surface wind field of the designed artificial water body by physical environment simulation analysis software, to obtain a wind disturbance region and a wind calm region of the designed artificial water body, so that an influence region and a prevention and control region of eutrophication of the designed artificial water body are preliminarily obtained, wherein the wind disturbance region is a major region where microalgae are generated, the wind calm region and downwind bays and tributaries are major regions where microalgae are generated and aggregated, the wind disturbance region is a prevention and control region of eutrophication of the designed artificial water body, and the wind calm region and downwind bays and tributaries are influence regions of eutrophication of the designed artificial water body.

For the artificial shallow-water type water bodies, wind disturbance is beneficial to the propagation of microalgae, however the movement and aggregation of microalgae will be formed by the wind because the microalgae is at the surface of the water and in a suspension state. Because of high wind velocity, microalgae will not aggregate on an open central water surface, and the aggregation of microalgae mainly occur in the downwind region, downwind bays and small-sized tributaries which are relatively wind-calm regions, for example, the region of Tai Lake with the most serious eutrophication is located in the north bay of the lake.

The distribution of a water body surface wind field can be obtained by the physical environment simulation analysis software, by analyzing the distribution of a water body surface wind field, a wind disturbance region (i.e., higher wind velocity) and a wind calm region can be obtained, wind disturbance region is a major region where microalgae are generated, the wind calm region and downwind bays and tributaries are major regions where microalgae are aggregated. The wind disturbance region is a prevention and control region of eutrophication of the designed artificial water body, and the wind calm region and downwind bays and tributaries are influence regions of eutrophication of the designed artificial water body. Therefore, the prevention and control region of eutrophication and the influence regions of eutrophication of the designed artificial water body can be obtained preliminarily.

Step S206: conducting temperature and microalgae propagation adaptability analysis on the designed artificial water body by simulating and analyzing the spatial distribution difference of water temperature of the designed artificial water body through the physical environment simulation analysis software so as to estimate the influence of the spatial distribution difference of the water temperature of the designed artificial water body on the distribution of microalgae inside the designed artificial water body.

Temperature has an adjustment effect on the intracellular metabolic process of microalgae at varying degrees. When the solar radiation and nutrients are in a saturation condition, different planktonic microalgae have different optimum and maximum growth temperatures, wherein the optimum growth temperature for blue-green algae is 25-35, the temperature range suitable for diatom is wide, and diatom can grow well at 15-35, preferably at 20-30.

By analyzing the influence of the spatial distribution difference of water temperature of the designed artificial water body on distribution of microalgae inside the designed artificial water body by the physical environment simulation analysis software, the possibility and degree of eutrophication of the designed artificial water body are preliminarily estimated. If the spatial distribution difference of temperature of the same water body is not obvious, the influence on the distribution of microalgae inside the designed artificial water body is not obvious either.

Step S207: determining corresponding strategies for preventing and controlling eutrophication of the designed artificial water body according to the possibility and severity of eutrophication of the designed artificial water body, and returning the adjustment to reevaluate, until the assessment result indicates that the high risk regions of eutrophication of the designed artificial water body are obviously reduced.

The water body eutrophication is represented by the excessive propagation of microalgae. In addition to the nutrient substances such as N, P. etc. in the water body which are required for the propagation of microalgae, solar radiation, temperature and wind disturbance can also have key effects to trigger the eutrophication. Because the water body is a designed artificial water body, the surrounding imported nutrient sources are not considered temporarily, only the disturbances generated by an internal mechanism of the aquatic ecosystem and the climate factors is analyzed.

In combination with the simulation result of the physical environment simulation analysis software, the eutrophication influence (microalgae aggregation) region and the eutrophication prevention and control (propagation of microalgae) region of the designed artificial water body can be obtained finally by comprehensively analyzing the water body depth, flow rate of the incoming water, microalgae species, water body temperature, solar radiation and form of the water body.

According to the possibility and severity of eutrophication of the designed artificial water body, an adjustment scheme can be proposed subsequently, and returned to the system to reevaluate, until the assessment result indicates that the high risk regions of eutrophication in the designed artificial water body are obviously reduced. For example, the form of the water body can be changed. The planning of bays and small-sized tributaries in the downwind direction region at main wind frequency should be avoided as far as possible in the peak period of eutrophication; alternatively, the height and layout of the surrounding buildings can be adjusted, the wind velocity of bays and small-sized tributaries can also be increased to reduce downwind calm-wind small-area regions.

If the risk of eutrophication of the designed artificial water body is still unavoidable after adjusting the scheme for many times, some corresponding strategies for controlling the risk of eutrophication of the designed artificial water body can also be proposed at a later construction design stage of the designed artificial water body, for example, an ecological water body restoration technology is adopted in the mass propagation and aggregation regions of microalgae in the water body, the nutrient substance of the water body is purified by using submerged, emergent and free-floating large-sized aquatic plants, and biomanipulation is conducted by stocking algophagous fish. In addition, the propagation of microalgae is suppressed by the interspecific competition principle, allowing the competition for nutrient substance and solar radiation between the macrophytes and microalgae.

In the embodiment of the present invention, by establishing the three-dimensional model of the designed artificial water body, and analyzing the designed artificial water body through an ecological simulation technology, at least one of the analysis results including hydrological mobility, hydraulic retention time, algae community composition of source water, designed water depth, water body surface wind field, solar radiation and temperature of the designed artificial water body can be obtained, whereby to evaluate the risk of eutrophication of the designed artificial water body. In this way, the risk assessment of eutrophication of the designed artificial water body in the urban planning and design can be done, whereby preventing and controlling the eutrophication of the designed artificial water body can be realized depending on the assessment results.

The method for early warning analysis of eutrophication of a designed artificial water body of the present invention will be explained by a specific example.

The designed artificial water body is located at Tengzhou City, Shandong Province, where in summer air pressure: 996.3 hpa; temperature: 26.0; wind: SSE, 2.2 m/s; water body temperature: 22; water depth: 5 m.

The physical environment simulation analysis software and modeling software are: Google Sketchup 7, Phoenics 2010 and EcotectAanalysis 2011.

The specific analysis of eutrophication of the designed artificial water body are as follows:

(1) Major eutrophication algae species: through the current situation investigation, within the planning region, eutrophication microalgae of the surrounding rivers is mainly filamentous algae, and the historical records of eutrophication near the lakes indicate that algal bloom of blue-green algae emerged in the past. The species of dominant eutrophication algae will be different due to different climate conditions and nutritional conditions.

(2) Hydraulic retention time and hydrological mobility: the area is 0.46 km$^2$, the hydraulic retention time is designed as 15 days, and the water body is a connective water area between two rivers and has good connectivity.

(3) Water depth and wind disturbance: shallow-water type lakes, with the mean water depth of 5 m; the wind disturbance is beneficial to the mixing of nutrients and the propagation of microalgae.

Figure 4:
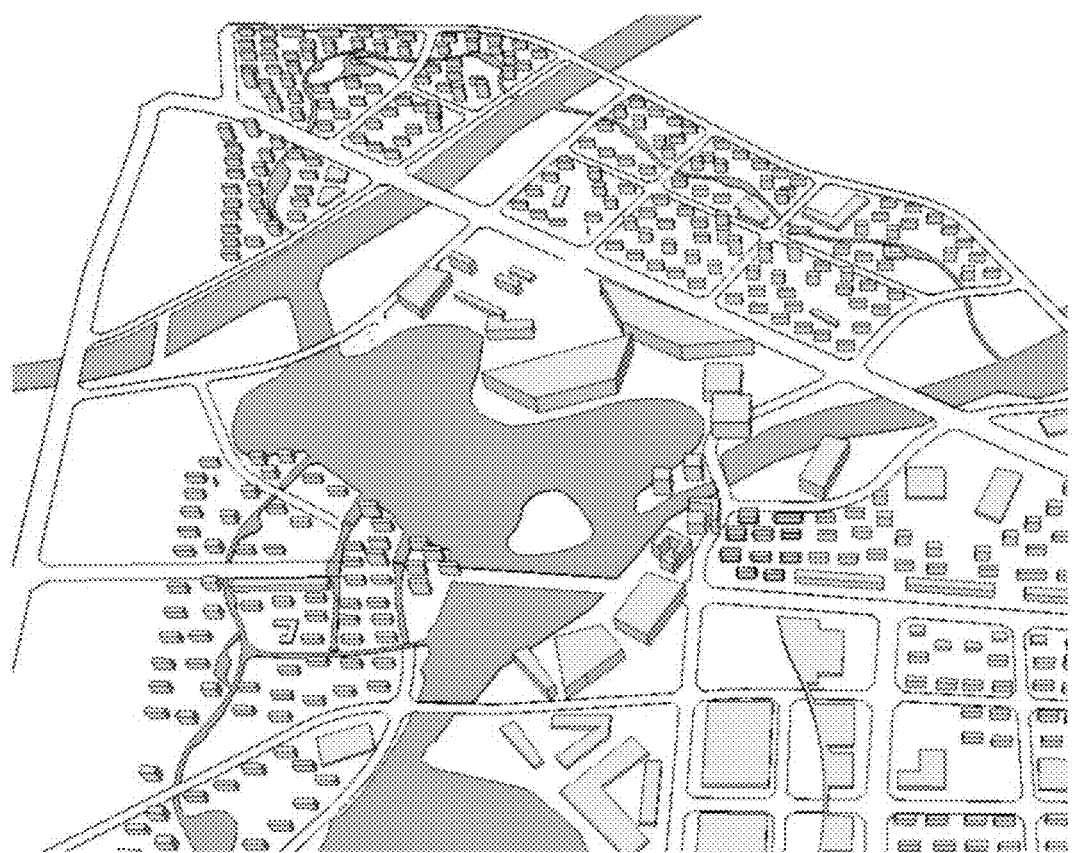
FIG. 4 is a three-dimensional model diagram of an original solution in a case based on a method for early warning analysis of eutrophication of a designed artificial water according to the present invention.

(4) Computation of physical environment simulation analysis software: a three-dimensional model with a modeling range of greater than the analysis range is established. The lake Sketchup model is shown in FIG. 4.

Figure 5:
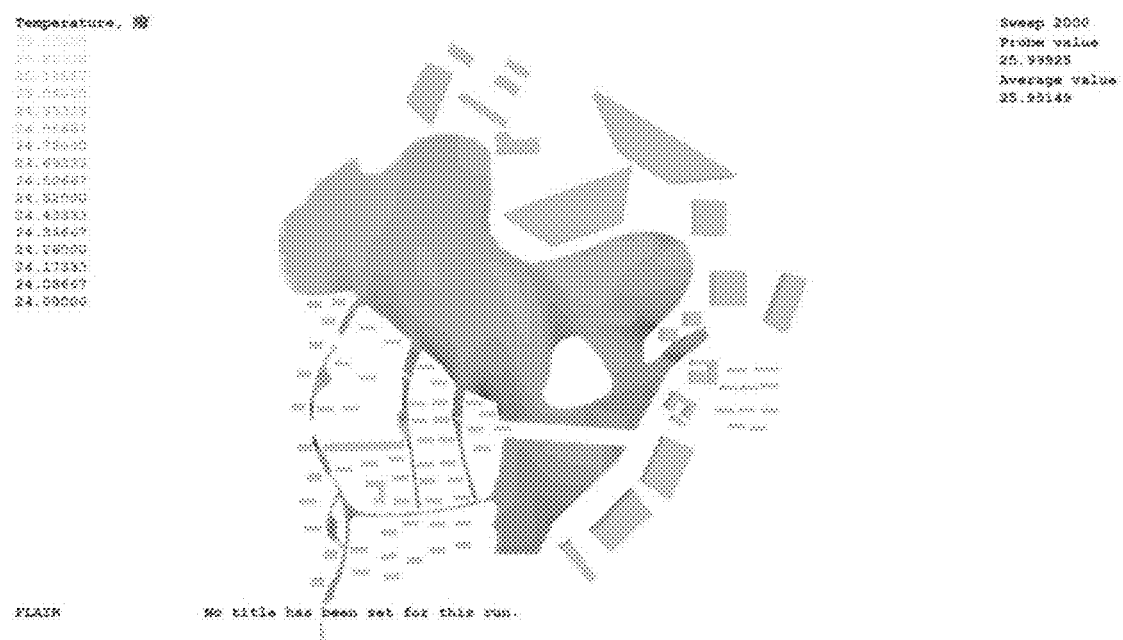
FIG. 5 is a schematic diagram of a result of physical environment simulation analysis software on a surface temperature of a lake of an original solution in a case based on a method for early warning analysis of eutrophication of a designed artificial water body according to the present invention.
Figure 6:
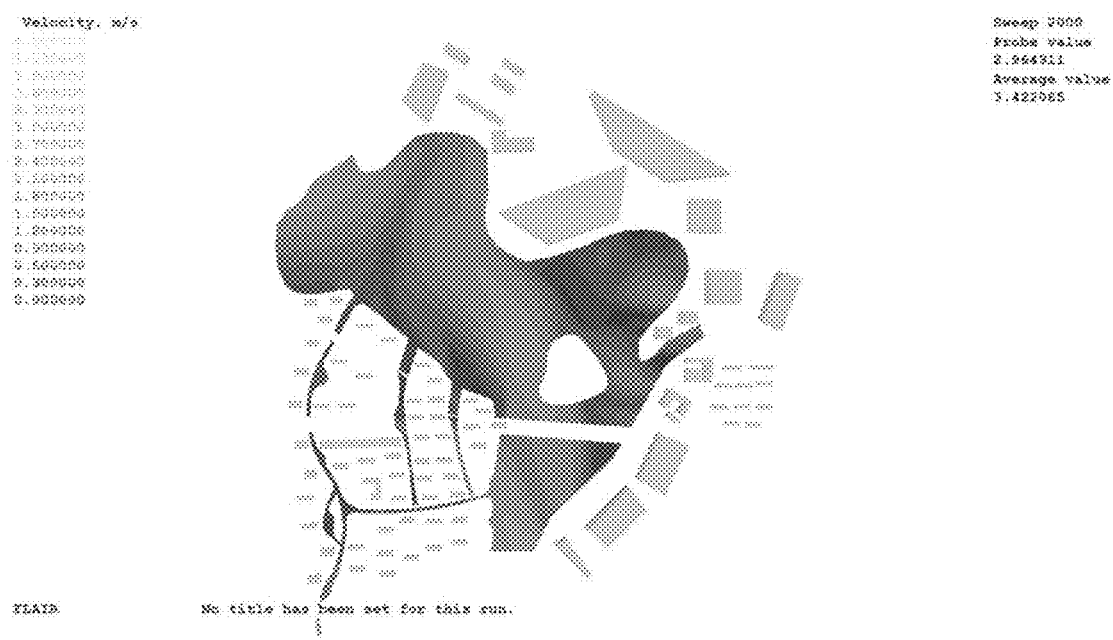
FIG. 6 is a schematic diagram of a result of physical environment simulation analysis software on a surface wind velocity of a lake of an original solution in a case based on a method for early warning analysis of eutrophication of a designed artificial water body according to the present invention.

The simulation result of the physical environment simulation analysis shows that: the surface temperature difference in various regions of the lake water body is not significant with a temperature difference of 1.2. The result of the physical environment simulation analysis software for the surface temperature of the lake is shown in FIG. 5, in which, the deeper the color is, the lower the temperature is. The wind velocity in the south-central lake water body is the fastest, up to 3.9 m/s, and decreases gradually towards the shore, the region with the slowest wind velocity appears at the slender tributary part in the southwest buildings and the northwest and east bays, the lake surface is basically static and was not subjected to wind disturbance. However, in this scheme, the range of wind calm regions is relatively wide, so that the possibility of algal bloom of blue-green algae is higher than that of the algal bloom of filamentous algae. In general, the damage of algal bloom of blue-green algae to ecology is relatively huge. The result of the physical environment simulation analysis software for the surface wind velocity of the lake is shown in FIG. 6, in which the deeper the color is, the lower the wind velocity is.

Figure 7:
FIG. 7 is a schematic diagram of a result of simulation analysis of surface solar radiation of a lake of an original solution in a case based on a method for early warning analysis of eutrophication of a designed artificial water body according to the present invention.

(5) Surface solar radiation of water body: the simulation analysis height is the height of the lake level. The number of floors of the surrounding buildings is 8-18, the lake area is large, the building area is small, and the shadowed range is thus relatively small. The lake surface solar radiation of the main water body is good, the southwest tributary is partially shadowed by the buildings, and the solar radiation proportion is 50%-80% (that is, the time of exposure to direct sunlight within annual solar radiation duration is 50%-80%). The result of simulation analysis of surface solar radiation of the lake is shown in FIG. 7, in which the deeper the color is, the lower the time scale for obtaining solar radiation is.

(6) Water body form and microalgae aggregation under wind field disturbance: the wind velocity in the south-central lake water body is the maximum, which can reach 3.9 m/s; the wind disturbance to the lake surface is relatively large, and the wind disturbance is beneficial to the formation of algal bloom of filamentous algae; the wind disturbance region is the major region where microalgae is generated, i.e. a prevention and control region of eutrophication of the designed artificial water body; the wind velocity is gradually reduced towards the shore, the region with the minimum wind velocity appears at the slender tributary part in the southwest buildings and the east and northwest bay regions. The lake surface is basically static and is not subjected to the wind disturbance. Algal bloom of blue-green algae may possibly emerge in the wind calm region with large area which belongs to the microalgae aggregation region, i.e. the influence region of eutrophication of the designed artificial water body.

(7) Temperature and microalgae propagation suitability: surface temperature difference in various region of the lake is minor, i.e. 24.0-25.2, the temperature difference is 1.2 and has minor influence on the distribution of microalgae.

Figure 8:
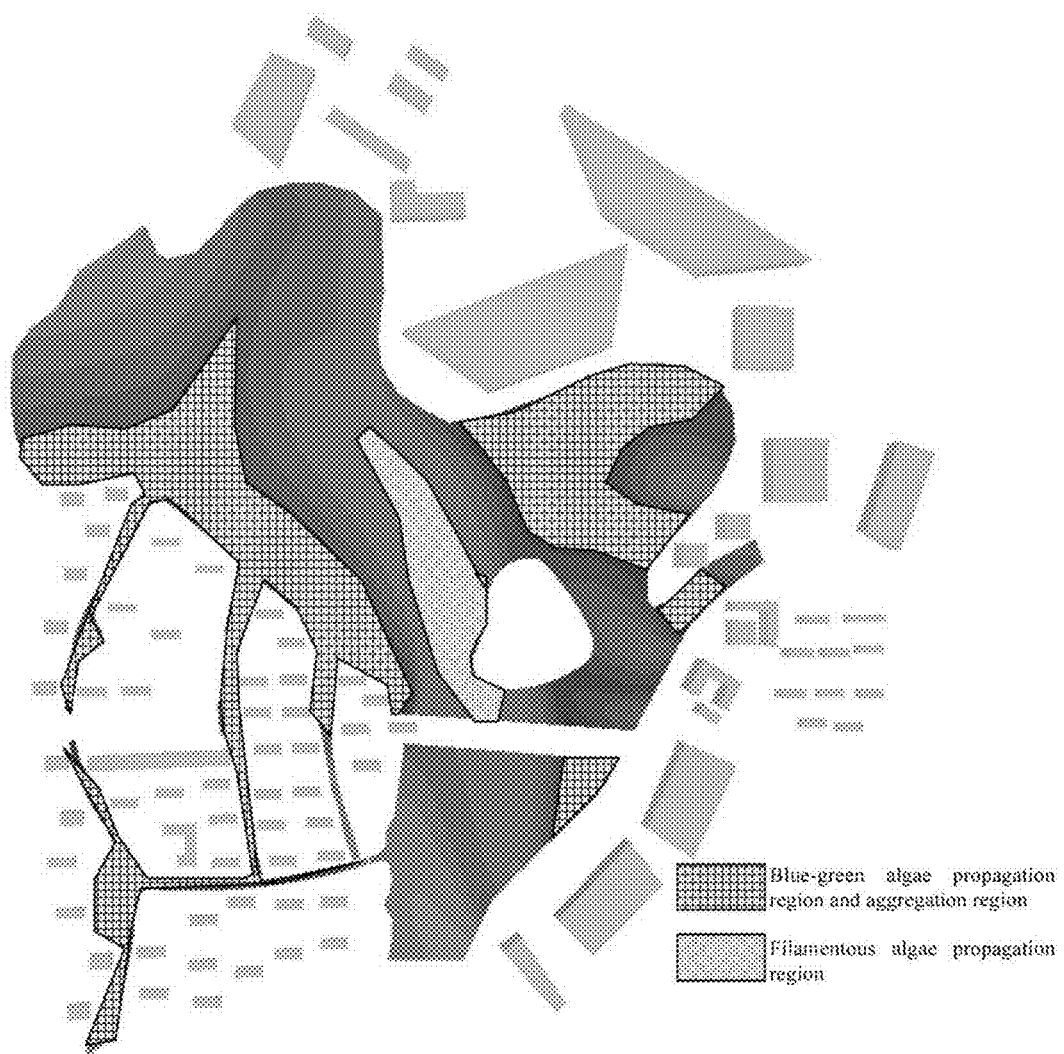
FIG. 8 is a schematic diagram of a reproduction and aggregation region of microalgae of an original solution in a case based on a method for early warning analysis of eutrophication of a designed artificial water body according to the present invention.

(8) Early warning range of high risk of eutrophication: through the above-mentioned comprehensive analysis, the mass propagation regions and aggregation regions of microalgae in planned lakes are obtained, as shown in FIG. 8.

Based on the above analysis, the scheme is adjusted by using the following measures: reducing the density of the buildings near the lakes, reducing the height of the buildings near the lakes, adjusting the facing direction of upwind buildings, reducing the bays and tributaries.

A specific eutrophication analysis for the designed artificial water body adjusted is as follows:

(1) Algae species, water depth, hydraulic retention time and hydrological mobility are analyzed in a way similar to the above.

Figure 9:
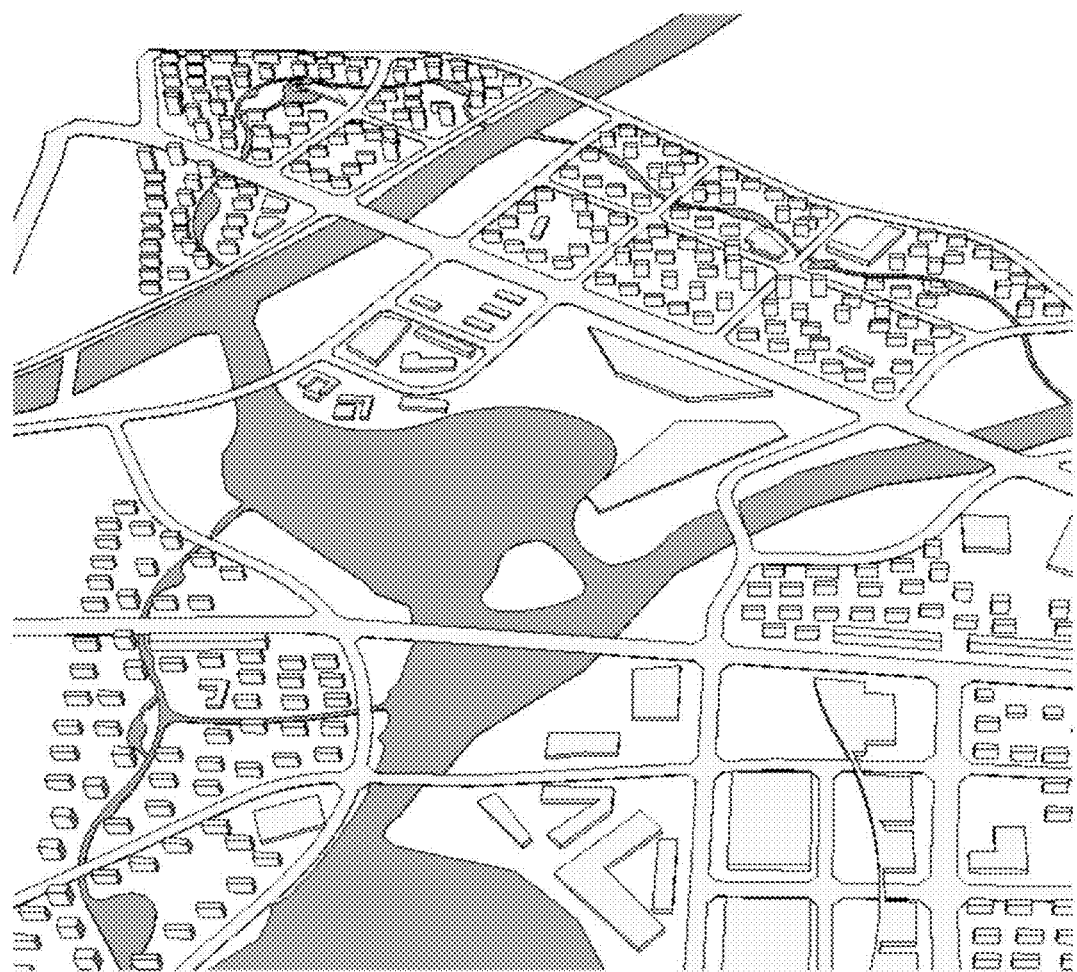
FIG. 9 is a three-dimensional model diagram of an adjustment solution in a case of a method for early warning analysis of eutrophication of a designed artificial water body according to the present invention.

(2) The three-dimensional modeling model is as shown in FIG. 9.

Figure 10:
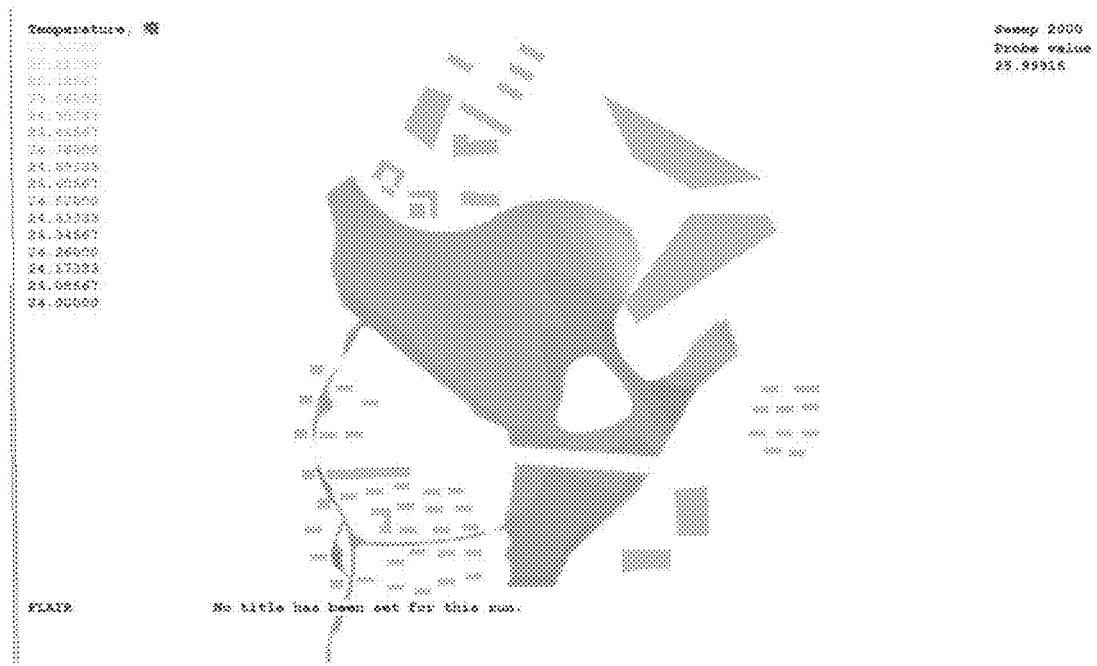
FIG. 10 is a schematic diagram of a result of physical environment simulation analysis software on a surface temperature of a lake water body of an adjustment solution in a case based on a method for early warning analysis of eutrophication of a designed artificial water body according to the present invention.
Figure 11:
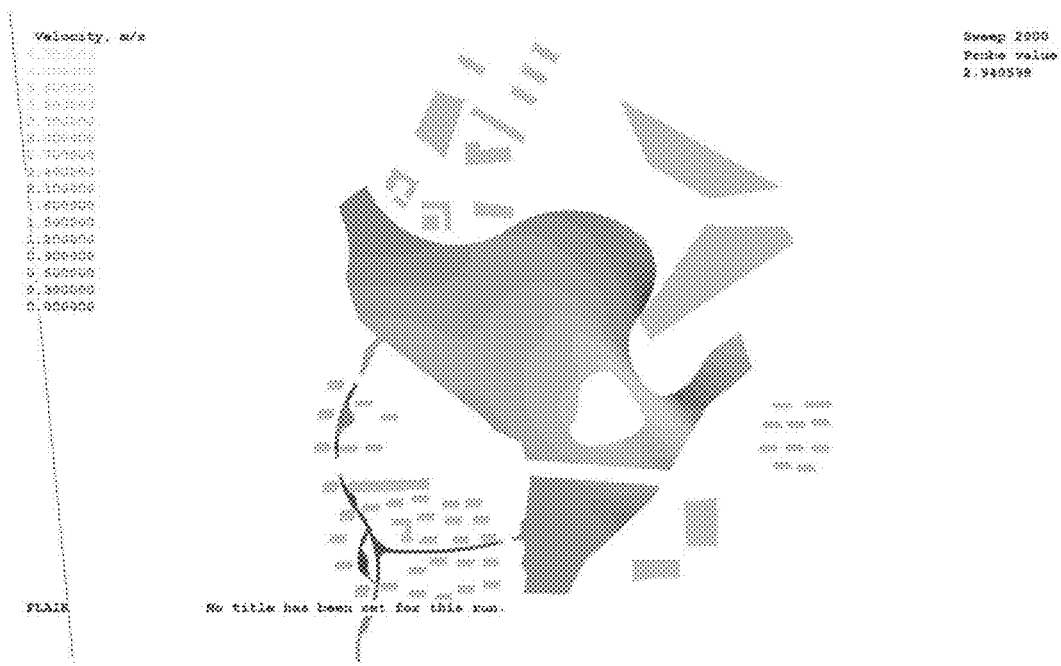
FIG. 11 is a schematic diagram of a result of physical environment simulation analysis software on a surface wind velocity of a lake water body of an adjustment solution in a case based on a method for early warning analysis of eutrophication of a designed artificial water body according to the present invention.

(3) The simulation result of the physical environment simulation analysis software shows that: the surface temperature difference of various regions of the lake is minor, and the temperature difference is 1.1. The result of the physical environment simulation analysis software of the surface temperature of the lake is shown in FIG. 10, in which the deeper the color is, the lower the temperature is. The wind velocity in the middle of the lake is the maximum, which can reach 4.2 m/s; the wind velocity is gradually reduced towards the shore, the region with the minimum wind velocity appears at the slender tributary part in the southwest buildings and leeward region of the northeast buildings. The lake surface is basically static and is not subjected to wind disturbance. In the adjusted scheme, the range of the wind calm regions is significantly reduced. The result of the physical environment simulation analysis software of the surface wind velocity of the lake is shown in FIG. 11, in which, the deeper the color is, the lower the wind velocity is.

Figure 12:
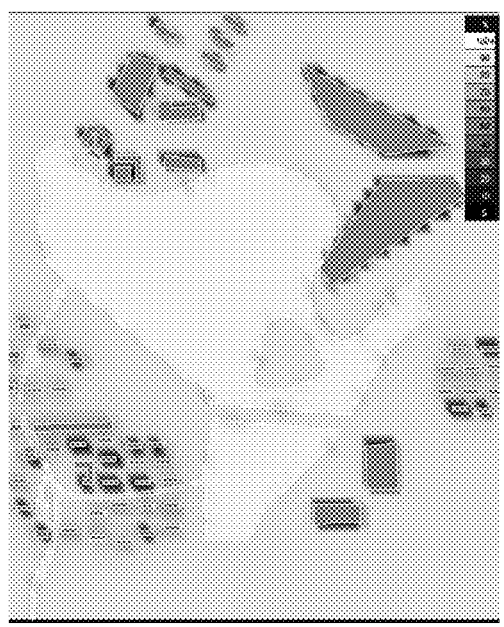
FIG. 12 is a schematic diagram of a result of simulation analysis of surface solar radiation of a lake water body of an adjustment solution in a case based on a method for early warning analysis of eutrophication of a designed artificial water body according to the present invention.

(4) Surface solar radiation of the water body: the number of floors of the surrounding buildings is 3-8, the lake surface is essentially not shadowed, and the lake surface solar radiation is good. The result of simulation analysis of surface solar radiation of the lake is shown in FIG. 12, in which, the deeper the color is, the lower the time scale of obtaining solar radiation is.

(5) Water body form and microalgae aggregation under the wind field disturbance: the wind velocity in the middle of the lake water body is the fastest, which can reach 4.2 m/s; the wind disturbance to the lake surface is relatively large, and the wind disturbance is beneficial to the formation of algal bloom of filamentous algae; the wind velocity decreases gradually towards the shore, the region with the slowest wind velocity appears at the slender tributary part in the southwest buildings and leeward region of the northeast buildings, and the lake surface is basically static and is not subjected to the wind disturbance. The north lake water body and the wind calm tributary are in the downwind direction of the dominant wind in summer, belonging to the microalgae aggregation regions, and it is still possible for algal bloom of blue-green algae to emerge in the tributary parts.

(6) Temperature and microalgae propagation suitability: temperature difference between various regions of the lake surface is not significant, i.e. 24.0-25.2, the temperature difference is 1.1 and has minor influence on the distribution of microalgae.

Figure 13:
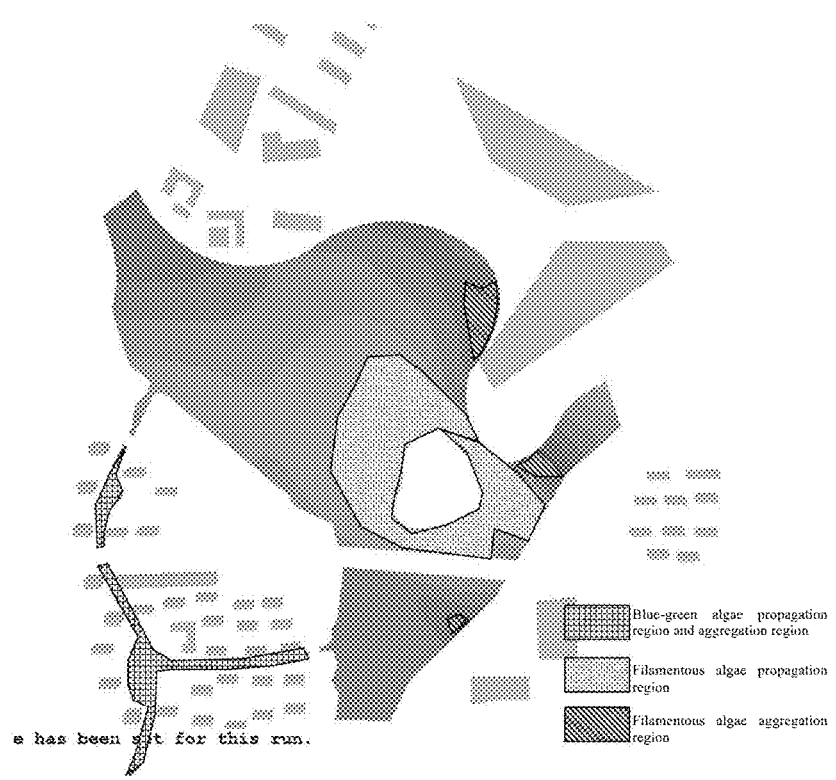
FIG. 13 is a schematic diagram of a reproduction and aggregation region of microalgae of an adjustment solution in a case based on a method for early warning analysis of eutrophication of a designed artificial water body of the present invention.

(7) Early warning range of high risk of eutrophication: upon the above-mentioned comprehensive analysis, the excessive propagation regions and aggregation regions of microalgae in the planned lakes are obtained, as shown in FIG. 13.

In conclusion, a comparative analysis of the two schemes is as follows:

The wind calm regions are significantly reduced in the adjusted scheme as compared with the original scheme, i.e. the possibility of harmful algal bloom of blue-green algae is greatly reduced. In addition, the algae aggregation regions are reduced, therefore it is easy to maintain the lake landscape.

For the adjusted scheme, in the aspect of application of ecological biotechnology, it is recommended to construct the artificial lake ecosystems with relatively complete components and structures in the excessive propagation regions and aggregation regions of filamentous algae and blue-green algae, for example, constructing macrophytic lakes, stocking an appropriate number of algophagous zooplankton and fish and configuring an appropriate number of shellfish, are all beneficial to the suppression of excessive microalgae propagation.

The above description is only the illustrative embodiments of the present invention, but not intended to limit the protection scope of the present invention. Any equivalent structures or flow transformations made by ways of the contents in the description and the drawings of the present invention, or direct and indirect application of the invention in other relevant technical fields shall fall into the scope of patent protection of the present invention.

What is claimed is:

1. A method for early warning analysis of eutrophication of a designed artificial water body, comprising the following steps:

establishing a three-dimensional model of a designed artificial water body according to data corresponding to a planning scheme of the water body, wherein the three-dimensional model of the designed artificial water body comprises at least the designed artificial water and surrounding buildings;

analyzing the designed artificial water body through an ecological simulation technology according to a three-dimensional model, to obtain at least one of the analysis results including mobility and hydraulic retention time, algae community composition of source water, designed water depth, water surface wind field, solar radiation and temperature of the designed artificial water body; and assessing the risk of eutrophication of the designed artificial water body according to at least one of the analysis results of ecological simulation.

2. The method of claim 1, wherein the step of analyzing the designed artificial water body through an ecological simulation technology according to the three-dimensional model comprises:

analyzing the distribution of a water body surface wind field of the designed artificial water body by physical environment simulation analysis software, to obtain a wind disturbance region and a wind calm region of the designed artificial water body, such that an influence region and a prevention and control region of eutrophication of the designed artificial water body are preliminarily obtained, wherein the wind disturbance region is a major region where microalgae are generated, the wind calm region and downwind bays and tributaries are major regions where microalgae are generated and aggregated, the wind disturbance region is a prevention and control region of eutrophication of the designed artificial water body, and the wind calm region and downwind bays and tributaries are influence regions of eutrophication of the designed artificial water body.

3. The method of claim 2, wherein the physical environment simulation analysis software includes Fluent, Phoenics, AirPak, CFDRC and Ecotect Analysis.

4. The method of claim 2, wherein if the assessment results indicate there are high risk regions of eutrophication existing in the designed artificial water body, the method further comprises:
   determining corresponding strategies for preventing and controlling eutrophication of the designed artificial water body according to the risk and severity of eutrophication of the designed artificial water body, and returning adjustments to reassess, until the assessment result indicates the high risk regions of eutrophication of the designed artificial water body are significantly reduced.

5. The method of claim 1, wherein the step of analyzing the designed artificial water body through an ecological simulation technology according to the three-dimensional model of the designed artificial water body comprising:
   conducting solar radiation analysis on the surface of the designed artificial water body by the physical environment simulation analysis software according to the simulation analysis of annual solar radiation and shadow variation, to obtain a region not shadowed by the surrounding buildings in the designed artificial water body, wherein the region not shadowed by the surrounding buildings in the designed artificial water body is an solar radiation region, i.e. an eutrophication-prone region.

6. The method of claim 5, wherein if the assessment results indicate there are high risk regions of eutrophication existing in the designed artificial water body, the method further comprises:
   determining corresponding strategies for preventing and controlling eutrophication of the designed artificial water body according to the risk and severity of eutrophication of the designed artificial water body, and returning adjustments to reassess, until the assessment result indicates the high risk regions of eutrophication of the designed artificial water body are significantly reduced.

7. The method of claim 5, wherein the physical environment simulation analysis software includes Fluent, Phoenics, AirPak, CFDRC and Ecotect Analysis.

8. The method of claim 1, wherein the step of analyzing the designed artificial water body through an ecological simulation technology according to the three-dimensional model of the designed artificial water body comprises:
   conducting analysis on the relationship between temperature and phytoplankton reproduction on the designed artificial water body; analyzing the spatial distribution difference of the water temperature of the designed artificial water body through the physical environment simulation analysis software, to determine the influence of the spatial distribution difference of the water temperature of the designed artificial water body on the distribution of phytoplankton in the designed artificial water body.

9. The method of claim 8, wherein if the assessment results indicate there are high risk regions of eutrophication existing in the designed artificial water body, the method further comprises:
   determining corresponding strategies for preventing and controlling eutrophication of the designed artificial water body according to the risk and severity of eutrophication of the designed artificial water body, and returning adjustments to reassess, until the assessment result indicates the high risk regions of eutrophication of the designed artificial water body are significantly reduced.

10. The method of claim 8, wherein the physical environment simulation analysis software includes Fluent, Phoenics, AirPak, CFDRC and Ecotect Analysis.

11. The method of claim 1, wherein the step of analyzing the designed artificial water body through an ecological simulation technology according to the three-dimensional model of the designed artificial water body comprises:
   conducting water body dominant phytoplankton species analysis on the designed artificial water body, specifically analyzing the dominant phytoplankton species from a water body around the designed artificial water body or a water body of a water source where eutrophication occurs and the corresponding climate condition, to obtain the potential microalgae species from the designed artificial water body where eutrophication may occur and the corresponding climate condition suitable for growth for the potential microalgae species.

12. The method of claim 11, wherein if the assessment results indicate there are high risk regions of eutrophication existing in the designed artificial water body, the method further comprises:
   determining corresponding strategies for preventing and controlling eutrophication of the designed artificial water body according to the risk and severity of eutrophication of the designed artificial water body, and returning adjustments to reassess, until the assessment result indicates the high risk regions of eutrophication of the designed artificial water body are significantly reduced.

13. The method of claim 1, wherein the step of analyzing the designed artificial water body through an ecological simulation technology according to the three-dimensional model of the designed artificial water body comprises:
   conducting hydrological mobility and hydraulic retention time analysis on the designed artificial water body, to estimate the possibility and degree of eutrophication of the designed artificial water body, wherein the designed artificial water body with a larger water body area has a higher threshold of the hydraulic retention time, and the designed artificial water body with a smaller water body area has a lower threshold of the hydraulic retention time; a flow rate of the designed artificial water body greater than 0.4 m/s indicates that the designed artificial water body is not eutrophication-prone, and a flow rate of the designed artificial water body less than or equal to 0.4 m/s indicates that the designed artificial water body is eutrophication-prone; and a relatively higher water body connectivity rate indicates that the designed artificial water body is less eutrophication-prone.

14. The method of claim 13, wherein if the assessment results indicate there are high risk regions of eutrophication existing in the designed artificial water body, the method further comprises:

determining corresponding strategies for preventing and controlling eutrophication of the designed artificial water body according to the risk and severity of eutrophication of the designed artificial water body, and returning adjustments to reassess, until the assessment result indicates the high risk regions of eutrophication of the designed artificial water body are significantly reduced.

15. The method of claim 1, wherein the step of analyzing the designed artificial water body through an ecological simulation technology according to the three-dimensional model of the designed artificial water body comprises:

conducting designed water depth and wind disturbance analysis on the designed artificial water body, to determine the influence of nutrients exchange in the designed artificial water body on the growth and reproduction of phytoplankton, wherein for a shallow-water type designed artificial water body, the wind disturbance is beneficial to the thorough mixing of nutrients at the top and the bottom of the designed artificial water body, and thus beneficial to the growth and reproduction of phytoplankton; however, for a deep-water type designed artificial water body, the wind would result in a temperature decrease and a disturbance of the still state of the surface water and then restrain the reproduction of phytoplankton in the water body.

16. The method of claim 7, wherein if the assessment results indicate there are high risk regions of eutrophication existing in the designed artificial water body, the method further comprises:

determining corresponding strategies for preventing and controlling eutrophication of the designed artificial water body according to the risk and severity of eutrophication of the designed artificial water body, and returning adjustments to reassess, until the assessment result indicates the high risk regions of eutrophication of the designed artificial water body are significantly reduced.

17. The method of claim 1, wherein the step of establishing the three-dimensional model of the designed artificial water body according to data corresponding to a planning scheme of the water body comprises:

by taking the designed artificial water body as an analysis range, extending a first distance from the boundary to the periphery, to determine a modeling range of the three-dimensional model, wherein the first distance is the distance from the water boundary to the center of the designed artificial water body; and establishing the three-dimensional model of the designed artificial water body by Sketchup, CAD or GIS software according to the bottom topography and the water body depth of the designed artificial water body, wherein the surface of the designed water body and the bottom of the surrounding buildings are at the same level.

18. The method of claim 17, wherein if the assessment results indicate there are high risk regions of eutrophication existing in the designed artificial water body, the method further comprises:

determining corresponding strategies for preventing and controlling eutrophication of the designed artificial water body according to the risk and severity of eutrophication of the designed artificial water body, and returning adjustments to reassess, until the assessment result indicates the high risk regions of eutrophication of the designed artificial water body are significantly reduced.

19. The method of claim 1, wherein if the assessment results indicate there are high risk regions of eutrophication existing in the designed artificial water body, the method further comprises:

determining corresponding strategies for preventing and controlling eutrophication of the designed artificial water body according to the risk and severity of eutrophication of the designed artificial water body, and returning adjustments to reassess, until the assessment result indicates the high risk regions of eutrophication of the designed artificial water body are significantly reduced.

* * * * *

UNITED STATES PATENT AND TRADEMARK OFFICE
CERTIFICATE OF CORRECTION

PATENT NO. : 10,387,586 B2  
APPLICATION NO. : 15/113595  
DATED : August 20, 2019  
INVENTOR(S) : Xiaojun Li et al.

Page 1 of 1

It is certified that error appears in the above-identified patent and that said Letters Patent is hereby corrected as shown below:

In the Claims

Column 19, Claim 16, Line 27, delete "7" and insert --15--.

Signed and Sealed this  
Nineteenth Day of November, 2019

Andrei Iancu  
*Director of the United States Patent and Trademark Office*